United States Patent [19]
Tsujimoto et al.

[11] 4,017,509
[45] Apr. 12, 1977

[54] PROCESS FOR PRODUCING SUBSTITUTED OR UNSUBSTITUTED 2-PHENYL-1.2.3.-TRIAZOLE-4-CARBOXALDEHYDE

[75] Inventors: Michihiro Tsujimoto, Tachikawa; Ryoichi Tsukahara, Yokohama; Masaaki Torisu, Tokyo; Ichiro Okubo, Hachioji, all of Japan

[73] Assignee: Mitsui Toatsu Chemicals, Incorporated, Tokyo, Japan

[22] Filed: Aug. 12, 1975

[21] Appl. No.: 604,031

[30] Foreign Application Priority Data

Sept. 2, 1974   Japan ............................. 49-99874

[52] U.S. Cl. .......................................... 260/308 A
[51] Int. Cl.$^2$ ...................................... C07D 249/06
[58] Field of Search ............................. 260/308 A

[56] References Cited
UNITED STATES PATENTS

| | | | |
|---|---|---|---|
| 3,637,673 | 1/1972 | Okubo et al. | 260/308 A |
| 3,891,632 | 6/1975 | Fleck et al. | 260/308 A |

OTHER PUBLICATIONS

Vargha et al., J. Chem. Soc., (London), 1951, pp. 1068–1069.
Riebsomer et al., J. Org. Chem., vol. 13, pp. 807–814, (1948).
Albert et al., J. Chem. Soc., Perkin Trans. I, 1973, pp. 1629–1633.
Drummond et al., J. Chem. Soc. (London), 1953, pp. 435–443.

*Primary Examiner*—Alton D. Rollins
*Attorney, Agent, or Firm*—Fisher, Christen & Sabol

[57] ABSTRACT

2-phenyl-1.2.3.-triazole-4-carboxaldehydes having the formula:

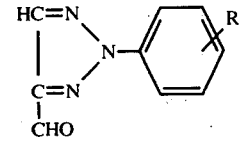

are obtained by oxidizing a 2-phenylglycosotriazole having the formula:

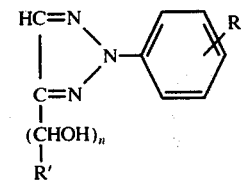

wherein R is hydrogen, halogen, methyl, carboxyl, a sulfonic acid group or the alkali metal salt thereof, *n* is 2 or 3, R' is hydroxymethyl when *n* is 2 and is hydroxymethyl or methyl when *n* is 3, with an oxide of manganese such as manganese dioxide or manganese oxide in dilute sulfuric acid of 20 to 80 wt. % concentration at a temperature of 0° to 80° C. The oxidation reaction is carried out in a dispersed state for from 2 to 100 hours and the resultant aldehyde is separated from the reaction mixture by extraction with an organic solvent. The purity of the aldehyde thus obtained is higher than 85 wt. % and the yield is 40% to quantitative on the basis of 2-phenylglycosotriazole. The aldehyde can be further purified by convenient means.

10 Claims, No Drawings

PROCESS FOR PRODUCING SUBSTITUTED OR UNSUBSTITUTED 2-PHENYL-1.2.3.-TRIAZOLE-4-CARBOXALDEHYDE

Background of the Invention

1. Field of the Invention

This invention relates to a process for producing substituted or unsubstituted 2-phenyl-1.2.3-triazole-4-carboxaldehydes. The aldehydes are important intermediates for dyestuffs, fluoroescent brighteners and other organic compounds.

2. Description of the Prior Art

Methods of preparation of 2-phenyl-1.2.3-triazole-4-carboxaldehydes are already known. The aldehydes are prepared through their oximes (Japanese Pat. No. 708,447), or obtained by the oxidation of 2-phenylglycosotriazoles using periodic acid as an oxidant (R. M. Hann and C. S. Hudson, J. Am. Chem. Soc., Vol. 66, Page 736 (1944)).

However, these prior art processes are very difficult to apply to commercial production of the aldehydes for several reasons. For example, in the method for preparing the aldehydes through their oximes, the oximes are very difficultly available because many reaction steps are required to obtain the oximes from such a starting material as citric acid as follows:

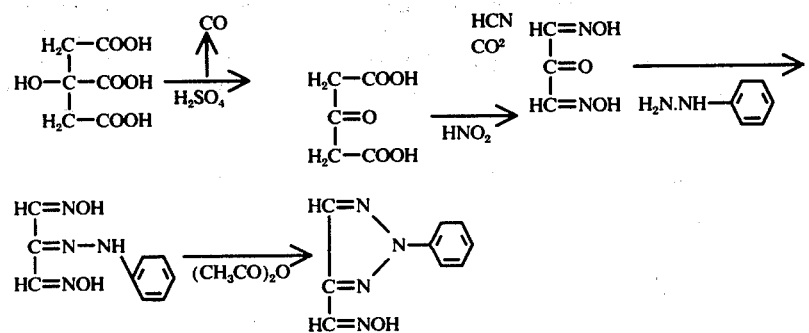

The intermediates in the above series of reactions are unstable, and some of the reaction steps above are accompanied by the evolution of such harmful gases as hydrogen cyanide or carbon monoxide, so that extreme caution and handling conditions are necessitated for preparation of the oximes in this manner.

On the other hand, the method for obtaining the aldehydes by the periodic acid oxidation of 2-phenylglycosotriazoles has the serious problem that the oxidant periodic acid is very expensive, and recovery of unreacted periodic acid from the reaction waste is very difficult.

Lead tetraacetate and bismuthate salts are known to be useful oxidants for the oxidation of 1,2-glycols into the corresponding aldehydes, and these oxidants can be also used for the oxidation of 2-phenylglocosotriazoles to produce the corresponding aldehydes. However, the commercial application of these oxidants in the production of the aldehydes is also very difficult because both lead tetraacetate and bismuthate salts are expensive and the recovery of unreacted lead tetraacetate or bismuthate salts from the reaction wastes is very difficult, and because use of the lead compound is restricted for purposes of prevention of environmental pollution.

On the other hand, oxides of manganese, for example, manganese dioxide or manganese oxide (trimanganese tetroxide) are well known oxidants for the oxidation of the methyl group or the hydroxymethyl group to an aldehyde group. However, it has not been known or disclosed that these oxides of manganese can be successfully used for the oxidation of 1,2-glycols to the corresponding aldehydes.

SUMMARY OF THE INVENTION

It is therefore an object of the present invention to provide a process for producing substituted or unsubstituted 2-phenyl-1.2.3-triazole-4-carboxaldehyde having the formula:

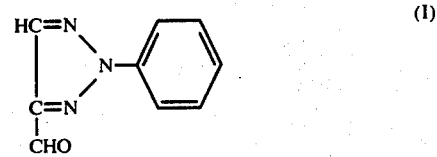

(I)

wherein R is a member selected from the group consisting of hydrogen, halogen, methyl, carboxyl, a sulfonic acid group or an alkali metal salt thereof.

The above object has been attained by the oxidation of a 2-phenylglycosotriazole having the formula:

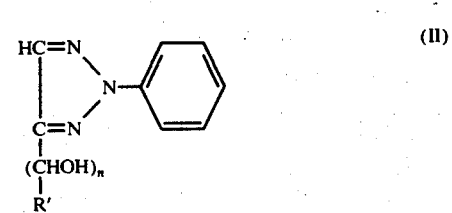

(II)

wherein R has the same meaning as that defined above in formula (I), $n$ is 2 or 3, R' is hydroxymethyl when $n$ is 2 and is methyl or hydroxymethyl when $n$ is 3, with an oxide of manganese such as manganese dioxide or manganese oxide in dilute sulfuric acid.

The resultant aldehyde is separated from the reaction mixture by extraction with an organic solvent. Then, the organic solvent is distilled away from the extract and the aldehyde is obtained. The thus obtained aldehyde can be further purified, if necessary, by a convenient purification method for aldehydes such as the purification method with a sodium bisulfite solution.

Description of the Preferred Embodiments

The 2-phenylglycosotriazoles which are used as starting materials for the process of the present invention can be obtained by the triazole cyclization of glycosazones of formula (V) prepared from monosaccharides of formula (III) and phenylhydrazines of formula (IV) as follows:

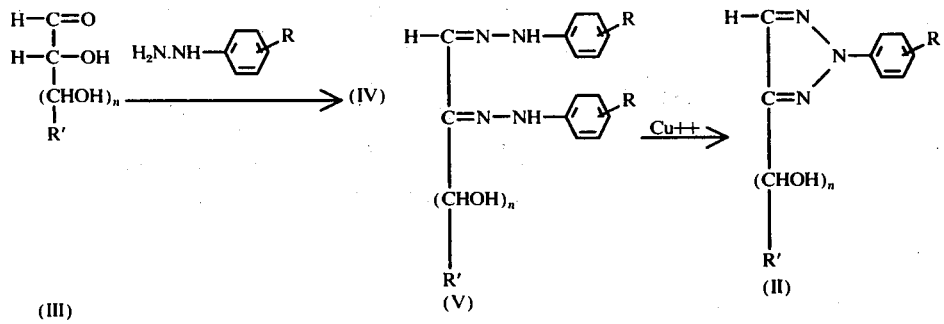

wherein the meanings of R, R' and $n$ in formulas (III), (IV) and (V) are the same as those defined for formula (II) hereinbefore.

Examples of the monosaccharides of formula (III) which can be employed in the present invention include D-glucose, D-mannose, D-galactose, L-arabinose, D-xylose and L-rhamnose. Examples of the phenylhydrazines of formula (IV) include m-chlorophenylhydrazine, p-chlorophenylhydrazine, p-bromophenylhydrazine, p-methylphenylhydrazine, p-carboxyphenylhydrazine, sodium phenylhydrazine-4-sulfonate and phenylhydrazine.

The structural formulas of the 2-phenylglycosotriazoles of formula (II) in which R is hydrogen are as follows:

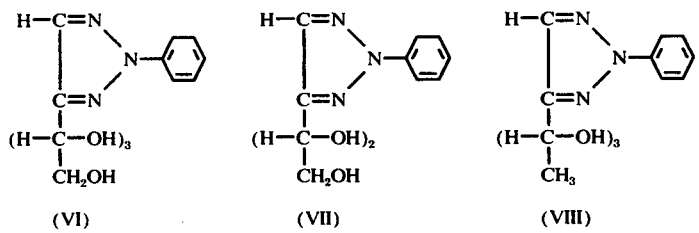

The 2-phenylglycosotriazoles are not completely dissolved in the dilute sulfuric acid, and are presented for the oxidation reaction in the dispersed state in the acid. Therefore, the 2-phenylglycosotriazoles are preferably finely pulverized by any convenient means before use so that the oxidation reaction will proceed smoothly.

The oxides of manganese useful as oxidant in the present invention are manganese dioxide and manganese oxide. The amount of the oxide of manganese is preferably within the range of from 3 to 8 moles, more preferably from 4 to 7 moles, per each 1 mole of the phenylglycosotriazole. The oxide is finely pulverized by any convenient means before use, if necessary or desired.

The concentration of the dilute sulfuric acid is generally within the range of from 20 to 80 wt. %, preferably from 30 to 50 wt. %. When using sulfuric acid with higher concentrations, e.g. above 60 wt. %, undesirable side reactions tend to be accelerated, and with sulfuric acid of lower concentrations, e.g. lower than 20 wt. %, the rate of the oxidation reaction is undesirably reduced. The amount of the dilute sulfuric acid (in terms of 100% sulfuric acid) is generally within the range of 5 to 30 parts by weight, preferably 5 to 20 parts by weight, for each part of the starting 2-phenylglycosotriazole.

In the present invention, the 2-phenylglycosotriazole and oxide of manganese are dispersed in the dilute sulfuric acid and the mixture is vigorously stirred. Thus, the oxidation reaction proceeds smoothly in the dispersed state. Suitable oxidation temperatures are generally within the range of from 0° to 80° C., preferably from 20° to 60° C. The application of higher reaction temperatures causes undesirable side reactions resulting in reduction of the yield.

The time required for the oxidation reaction is generally within the range of from 2 to 100 hours under such reaction conditions as described above with reference to the amount of the oxide of manganese, the reaction temperature and the concentration of sulfuric acid. A longer reaction time at a lower reaction temperature is preferred since it will depress undesirable side reactions and produce the aldehyde in a higher yield. Within the above period of reaction time, the essential consideration that the oxidation of the 2-phenylglycosotriazole into the corresponding aldehyde is substantially completed will be accomplished.

The resultant 2-phenyl-1.2.3-triazole-4-carboxaldehyde can be separated from the reaction mixture as follows:

The reaction mixture is extracted with an organic solvent such as ether, petroleum ether, benzene, toluene, xylene, ethylene dichloride, trichloroethylene, tetrachloroethylene, etc., then the organic solvent is distilled away from the extract by distillation, by distillation under reduced pressure or by steam distillation. In this manner, 2-phenyl-1.2.3-triazole-4-carboxaldehyde with a purity higher than 85 wt. % can be obtained.

The obtained 2-phenyl-1.2.3-triazole-4-carboxaldehyde can be further purified, if necessary, by any well known purification method for aldehydes, for example, purification with sodium bisulfite solution as described in Example 1.

In Table 1, the melting points of several substituted and unsubstituted 2-phenyl-1.2.3-triazole-4-aldehydes obtained according to the present invention are shown, although the invention is not limited thereto.

Table 1

| R | Melting Point (° C.) |
|---|---|
| -H | 70 |
| -CH$_3$(P) | 80–82 |
| -Cl (P) | 121 |
| -Cl (m) | 88–89 |
| -COOH (P) | 276–278 |
| -SO$_3$H (P) | >360 |

After the aldehyde is separated from the reaction mixture by extraction, the unreacted oxide of manganese remaining dispersed in the reaction mixture is easily recovered by filtration.

Industrial advantages of the present invention include the fact that the oxides of manganese are readily and cheaply available and are recovered quite easily from reaction mixture. The equivalent weights of the oxides of manganese, especially the equivalent weight of manganese dioxide, are smaller than those of oxidants employed by the prior art such as, for example, periodic acid, lead tetraacetate or bismuthate salts, so that in the present invention, it is possible to carry out the oxidation with a smaller amount of oxidant compared to the processes of the prior art.

Moreover, Mn++ is easily removed from the reaction waste water when the waste water, containing sulfuric acid and Mn++, is neutralized with an alkali and the resulting precipitate is filtered off. Thus, for example, waste waters containing only 0.38 ppm or 0.05 ppm of Mn++ are obtained by neutralization with sodium hydroxide or by neutralization with lime, respectively.

The advantages described above are valuable facets of the present invention with regard to prevention of environmental pollution.

The present invention will be particularly illustrated by the following non-limiting examples.

EXAMPLE 1

A mixture of 5.3 g. of 2-phenylglucosotriazole, 100 ml. of 50 wt. % sulfuric acid and 10.4 g. of manganese dioxide powder (75 wt. % purity) were stirred at 40° C. for 5 hours. Then, the reaction mixture was diluted with 100 ml. of water and was extracted with 100 ml. of ether. The ether was distilled away from the extract and the residue was dissolved in 50 ml. of boiling sodium bisulfite water solution containing 5% by weight sodium bisulfate. The solution was filtered to remove insoluble material and the resultant filtrate was basified with 10 ml. of 10% by weight aqueous sodium hydroxide to cause precipitation. The resultant precipitate was separated from the solution by filtration, washed with 50 ml. of water and dried. Thus, 2-phenyl-1.2.3-triazole-4-carboxaldehyde was obtained in 70% yield on the basis of 2-phenylglucosotriazole.

EXAMPLE 2

Example 1 was repeated except that the concentration of sulfuric acid and the reaction temperature were 65 wt. % and 20° C. instead of 50 wt. % and 40° C., respectively. 2-Phenyl-1.2.3-triazole-4-carboxaldehyde was obtained in a 40% yield, and at the same time the formation of a resinous by-product was observed.

EXAMPLE 3

Example 1 was repeated except that the concentration of sulfuric acid and the reaction temperature were 30 wt. % and 60° C. instead of 50 wt. % and 40° C., and that finely pulverized 2-phenylglucosotriazole was used. 2-Phenyl-1.2.3-triazole-4-carboxaldehyde was obtained in a quantitative yield.

EXAMPLE 4

A mixture of 5.3 g. of 2-phenylglucosotriazole, 100 ml. of 45% sulfuric acid and 10.4 g. of manganese dioxide powder (75 wt. % purity) were stirred at 30° C. for 48 hours. Then, the reaction mixture was diluted with 100 ml. of water and was extracted with 50 ml. of benzene. After evaporation of benzene from the extract, 2-phenyl-1.2.3-triazole-4-carboxaldehyde with purity higher than 85 wt. % was obtained in 80% yield. The thus obtained aldehyde, without further purification, can be employed for practical uses for which the purified aldehyde is commonly employed.

EXAMPLES 5–7

Example 1 was repeated except that 2-(P-chlorophenyl)-glucosotriazole, 2-(P-methylphenyl) glucosotriazole and 2-(P-carboxyphenyl) glucosotriazole were respectively used instead of 2-phenylglucosotriazole. Thus, 2-(P-chlorophenyl)-1.2.3-triazole-4-carboxaldehyde, 2-(P-methylphenyl)-1.2.3-triazole-4-carboxaldehyde and 2-(P-carboxyphenyl)-1.2.3-triazole-4-carboxaldehyde were obtained respectively in similar yields as that of 2-phenyl-1.2.3-triazole-4-carboxaldehyde in Example 1.

EXAMPLES 8–11

Example 1 was repeated except that 2-phenylgalactosotriazole was used instead of 2-phenylglucosotriazole, and 2-phenyl-1.2.3-triazole-4-carboxaldehyde was obtained in a similar yield to that in Example 1. Example 1 was further repeated except that 2-phenylxylosotriazole, 2-phenylarabinosotriazole and 2-phenylrhamnosotriazole were respectively used instead of 2-phenylglucosotriazole, and that the amount of manganese dioxide was 8 g. instead of 10.4 g. 2-phenyl-1.2.3-triazole-4-carboxaldehyde was obtained in each example in a similar yield to that in Example 1.

As described hereinbefore, the 2-phenyl-1.2.3-triazole-4-carboxaldehyde produced according to the present invention are important intermediates for dyestuffs, fluorescent brighteners and other organic compounds. For example, such compounds as

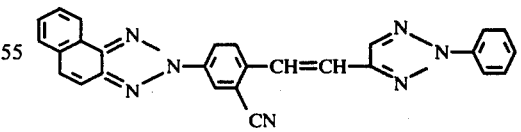

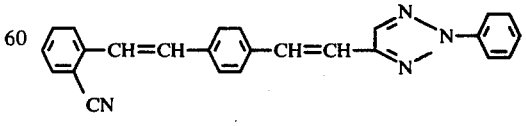

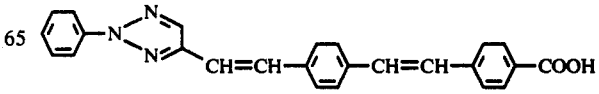

are valuable fluorescent brighteners for polyester fibers.

What is claimed is:

1. A process for producing substituted or unsubstituted 2-phenyl-1.2.3-triazole-4-carboxaldehyde having the formula:

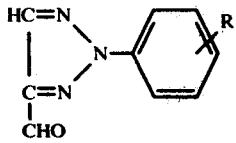

wherein R is hydrogen, halogen, methyl, carboxyl, sulfonic acid group or alkali metal salt thereof, which comprises oxidizing 2-phenylglycosotriazole having the formula:

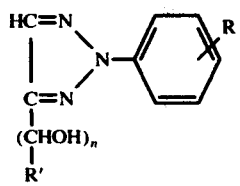

wherein R has the same meaning as that defined above, $n$ is 2 or 3, and R' is hydroxymethyl when $n$ is 2, and is methyl or hydroxymethyl when $n$ is 3, in dilute sulfuric acid with an oxide of manganese selected from the group consisting of manganese dioxide and manganese oxide.

2. The process according to claim 1 wherein said 2-phenylglycosotriazole is 2-phenylglucosotriazole.

3. The process according to claim 1 wherein said oxide of manganese is manganese dioxide.

4. The process according to claim 1 wherein said dilute sulfuric acid has a concentration of from 20 to 80 wt. %.

5. The process according to claim 4 wherein said dilute sulfuric acid has a concentration of from 30 to 50 wt. %.

6. The process according to claim 1 wherein the oxidation is carried out within a temperature range of from 0° to 80° C.

7. The process according to claim 6 wherein the oxidation is carried out within a temperature range of from 20° to 60° C.

8. The process according to claim 1 wherein said oxide of manganese is present in an amount of from 3 to 8 moles per mole of 2-phenylglycosotriazole.

9. The process according to claim 1 wherein the reaction mixture is extracted with an organic solvent and the organic solvent is then removed to yield the substituted or unsubstituted 2-phenyl-1.2.3-triazole-4-carboxaldehyde of high purity.

10. The process according to claim 1 wherein the oxidation is conducted in the dispersed state.

* * * * *